United States Patent

Oren et al.

[11] Patent Number: 6,037,503
[45] Date of Patent: Mar. 14, 2000

[54] PROCESS FOR THE PREPARATION OF PARA-FLUOROPHENOL

[75] Inventors: Jakob Oren, Nesher; Michel Adda, Kfar-Saba, both of Israel

[73] Assignee: Bromine Compounds Ltd., Israel

[21] Appl. No.: 09/101,631

[22] PCT Filed: Jan. 14, 1997

[86] PCT No.: PCT/IL97/00019

§ 371 Date: Jul. 14, 1998

§ 102(e) Date: Jul. 14, 1998

[87] PCT Pub. No.: WO97/26235

PCT Pub. Date: Jul. 24, 1997

[30] Foreign Application Priority Data

Jan. 15, 1996 [IL] Israel ......................................... 116759

[51] Int. Cl.[7] ............................. C07C 39/30; C07C 39/32
[52] U.S. Cl. .......................... 568/777; 568/774; 568/775; 568/778
[58] Field of Search ................................... 568/775, 774, 568/778; 570/127, 143, 190

[56] References Cited

U.S. PATENT DOCUMENTS

| | | | |
|---|---|---|---|
| 2,934,569 | 4/1960 | Kuehlewind, Jr. ..................... | 260/623 |
| 2,950,325 | 8/1960 | Britton et al. ......................... | 260/623 |
| 4,940,821 | 7/1990 | Pews et al. ............................. | 568/775 |

FOREIGN PATENT DOCUMENTS 34 30 554 A1  2/1986  Germany .
850888  10/1960  United Kingdom .

OTHER PUBLICATIONS

Journal of Organic Chemistry, vol. 26, No. 11, Nov. 1961, Washington, D.C., pp. 4641–4645, XP002030172, M. M. Boudakian et al., Aromatic Fluorine Compounds. II. Synthesis of p–Fluorophenol by the Selective Hydrolysis of p–Bromofluorobenzene.

Chemical Abstracts, vol. 57, No. 8, Oct. 15, 1962, Columbus, Ohio; abstract No. 9744b, XP002030173 & SU 143 404 A, N.N. Vorontsonv, Jr., et al.

*Primary Examiner*—Gary Geist
*Assistant Examiner*—Sreeni Padmanabhan
*Attorney, Agent, or Firm*—Lerner, David, Littenberg, Krumholz & Mentlik, LLP

[57] ABSTRACT

A process for the preparation of p-fluorophenol, which comprises hydrolyzing p-bromofluorobenzene with a mixture of NaOH and $Na_2CO_3$ in the presence of a copper catalyst.

17 Claims, No Drawings

PROCESS FOR THE PREPARATION OF PARA-FLUOROPHENOL

This is the U.S. National Stage Application of PCT/IL97/00019 filed Jan. 14, 1997 now WO97/26235 published Jul. 24, 1997.

1. Field of the Invention

This invention relates to a process for the preparation of p-fluorophenol by the hydrolysis of p-bromofluorobenzene. It particularly refers to a process which yields highly pure p-fluorophenol, obtained from a crude p-fluorophenol reaction product, which has an extremely low content of phenol and a low content of heavy by-products.

2. Background of the Invention

Aromatic fluorine compounds based on fluorobenzene are important intermediates for the manufacture of agrochemicals, pharmaceuticals and speciality polymers. One such fluorine compound is p-fluorophenol (hereinafter PFP). Various processes for the preparation of PFP are known in the art. Among them the following may be cited: direct fluorination of phenol, fluorination of p-aminophenol, hydroxylation of fluorobenzene, diazotization of p-fluoroaniline followed by hydrolysis of the diazonium salt, dealkylation of fluoroanisole or fluorophenetole, and hydrolysis of p-chlorofluorobenzene. A process which has received considerable attention in the art is the hydrolysis of p-bromofluorobenzene (hereinafter PBFB). Said hydrolysis has been carried out under basic conditions, under pressure, with or without a catalyst. The problems inherent in the preparation of PFP by the hydrolysis of PBFB are the low selectivity regarding PFP and the formation of phenol by-product. Phenol is not the only by-product formed; other by-products are, for instance, 4,4'-difluorodiphenyl ether (hereinafter DFDPE) and 4-fluoro-4'-hydroxydiphenyl ether (hereinafter FHDPE). Phenol, however, is a particularly undesirable by-product, because it is practically impossible to remove by distillation, and other methods known for its removal, such as melt crystallization or treatment with phthalic anhydride/$H_2SO_4$, require an extra process step, which is detrimental to the economics of the process. Therefore considerable attention has been devoted in the art to the reduction of the amount of phenol formed, but the results have not been completely satisfactory.

Thus, U.S. Pat. No. 2,934,569 and GB 850888 disclose the hydrolysis of PBFB with $Ca(OH)_2$ as a base, and in the presence of a catalyst, whereby it is attempted to reduce the formation of phenol, but PFP is obtained in yields of only 50–70% and large amounts of DFDPE (10–15%) are formed.

Russian Patent 143404 describes the hydrolysis of PBFB using an alkali fluoride, such as $NaHF_2$ or KOAc, as a base and $Cu_2O$ as the catalyst. The reaction takes place at 250° C. for 4 hours with a PFP yield of 73%.

DE 3430554 discloses the hydrolysis of PBFB in the presence of $Ba(OH)_2$ with Cu powder as a catalyst and a quaternary ammonium cocatalyst. Yields of up to 94.6% are mentioned.

U.S. Pat. No. 2,950,325 describes the basic hydrolysis of PBFB with alkaline earth metal oxides or hydroxides, which are said to avoid the formation of by-products such as phenol, "which are frequently formed when the stronger alkaline agent, e.g., potassium hydroxide or sodium hydroxide, is employed in the reaction".

In conclusion, the prior art teaches that the best way of carrying out the basic hydrolysis of PBFB comprises using a copper compound catalyst, and calcium or barium hydroxide as a base. Stronger bases, such as in particular sodium hydroxide, are said to produce bad results. The combined use of calcium hydroxide and copper catalysts, according to prior art, provides yields that may reach 70–75%.

It is a purpose of this invention to provide a process for the production of PFP which gives this product in high yields and a very low amount of phenol by-product.

It is a particular purpose of this invention to provide such a process which comprises the hydrolysis of PBFB and permits a reduction in the formation of phenol to amounts in the order of 0.1% and even below that amount.

It is a further purpose of this invention to provide such a process which does not involve the production of large amounts of heavy by-products, such as DFDPE and FHDPE. Any such heavy by-products are easily removed during the work-up, which includes extraction with an organic solvent, followed by fractional distillation.

It is a still further purpose of this invention to achieve the aforesaid purposes by a simple and economical process, which does not involve the use of expensive reagents.

It is a still further purpose of this invention to provide a process for the production of PFP having increased productivity together with high selectivity.

Other purposes and advantages of this invention will appear as the description proceeds.

SUMMARY OF THE INVENTION

The process according to the invention is characterized in that PBFB is hydrolyzed with a mixture of NaOH and $Na_2CO_3$ as the base, and using a copper catalyst.

It is known that the use of NaOH alone as base produces PFP with a phenol content of ~0.7%. We have found that under the preferred conditions, the hydrolysis with NaOH together with $Na_2CO_3$ as the base, succeeded in producing PFP with a lower amount of phenol and a relatively low amount of heavy by-products relative to the prior art processes.

The hydrolysis is carried out on pure PBFB at temperatures from 180 to 240° C., and preferably at a temperature of 200–210° C. An increase in the temperature leads to an increase in the rate of the reaction, but also to an increase in the amount of phenol formed and the amount of $F^-$ in the reaction mixture. A lower temperature increases the reaction time.

The molar ratio NaOH/PBFB is comprised between 0.8 and 2.6, and preferably between 1.4 and 2.4. The $Na_2CO_3$/PBFB molar ratio is comprised between 0.25 and 1.6, and preferably between 0.25 and 1.2. The copper catalyst is chosen from among $Cu_2O$, CuO and $CuSO_4 \cdot 5H_2O$, and is preferably an oxide, $Cu_2O$ or CuO. The molar ratio of PBFB to $Cu_2O$ is from 4 to 16 and the molar ratio of PBFB to CuO is from 2 to 8.

DETAILED DESCRIPTION OF PREFERRED EMBODIMENTS

When the reaction is carried out in a batch process, the NaOH and $Na_2CO_3$ are used in aqueous solution and the total base concentration (NaOH+Na$_2$CO$_3$) in said solution varies from 10 to 30% and preferably from 20 to 25% w/w. The preferred molar ratio NaOH/PBFB is comprised between 1.4 and 1.6. The preferred Na$_2$CO$_3$/PBFB molar ratio is comprised between 1.1 and 1.2. The bases are charged together with the PBFB and the catalyst into a reactor, which is sealed and heated to reaction temperature for the required period of time. The use of a higher concentration of base raises the efficiency of the reactor, but as the base concentration increases, more phenol and heavy by-products (DFDPE and FHDPE) are formed. Thus, NaOH/PBFB in a molar ratio of ~1.4, together with Na$_2$CO$_3$/PBFB in a molar ratio of ~1.1, gave a product with a low amount of phenol (~0.1%) and relatively low amounts of heavy by-products (~6–8%).

The preferred molar ratio of PBFB to Cu$_2$O is between 6 and 12, and the preferred molar ratio of PBFB to CuO is between 3 and 6. The larger amounts of catalyst accelerate the reaction and reduce the formation of phenol by-product.

The reaction time is about four hours at 205±5° C. Under the aforesaid conditions, low amounts of phenol and heavy by-products are obtained, with high conversions of PBFB (>99.5%). PFP yields of 85–90%, before distillation, are achieved.

The reaction product is subjected to work-up, comprising filtration of the reaction mixture, acidification to pH 3–7 with concentrated aqueous HCl, then extraction with an organic solvent. The solvent is chosen from among toluene, n-butyl acetate (n-BuAc) and methyl isobutyl ketone (MIBK).

The organic phases from the extraction are combined and subjected to fractional distillation. The fractional distillation is carried out with about 5–10 theoretical stages and the pure PFP comes off at 123–125° C. at 100 mm Hg.

The foregoing advantages of the invention may be better understood through the following illustrative and non-limitative examples.

Examples 1 to 23 illustrate embodiments in which the invention is carried out in a batch process.

EXAMPLE 1

Preparation of PFP using a mixture of Na$_2$CO$_3$ and NaOH as the base

A one liter autoclave was charged with 620 g water, 50.6 g NaOH (1.26 mol), 105.2 g Na$_2$CO$_3$ (0.99 mol), 157.5 g pure PBFB (0.9 mol) and 11 g Cu$_2$O (0.076 mol). The autoclave was sealed and heated to 205° C. over 45 minutes, then maintained at 205° C. for 4 hrs. The contents of the autoclave were cooled to room temperature and filtered. The composition of the reaction mixture was determined by GC and GC/MS.

The conversion of the PBFB, determined by titrating the filtrate for Br$^-$, was >99.5%. The filtrate was carefully acidified with 188 g 32% HCl to pH 3–7 and extracted with 2×250 g toluene.

Four experiments were carried out under these conditions. The extraction was performed counter-current, i.e. organic phase from the second extraction served as the extractant for the first extraction of the following batch.

All the organic phases were combined and then distilled in a laboratory column, 1" diameter, about 5 theoretical stages. The solvent was distilled at atmospheric pressure, and can be recycled. Fractional distillation was then performed. The pure PFP was obtained at 123–125° C. at 100 mm Hg. The main fraction contained 320 g PFP in a purity of 99.5% and a phenol content of 0.1%. Off-spec fractions containing ~25 g PFP can be transferred to the next distillation.

Based on these results, the yield of PFP is ~85%, based on starting PBFB.

EXAMPLES 2 AND 3

The preparation of PFP was carried out as described in Example 1, but under the following conditions and with the results shown in Table I:

aq. (NaOH+Na$_2$CO$_3$)—20%
NaOH/PBFB molar ratio—1.4
Na$_2$CO$_3$/PBFB molar ratio—1.1
PBFB/Cu$_2$O molar ratio—6.0
Temperature—205±5° C.
Time—4 hours

TABLE I

| Example No. | Composition (GC, area %)* | | | | | F$^-$ in aq. reaction mixture | |
|---|---|---|---|---|---|---|---|
| | FB | PBFB | PFP | DFDPE | FHDPE | ppm | mole % |
| 2 | 1.1 | 0.1 | 94.0 | 2.9 | 1.7 | 770 | 4.2 |
| 3 | 1.6 | 0.2 | 92.8 | 3.0 | 1.6 | 700 | 3.8 |

*PhOH n.d. < 0.1%

It should be pointed out that under said conditions, the level of F$^-$ in the reaction mixture is ~700–800 ppm, which is lower than obtained with the use of NaOH alone. The yield of PFP in the crude reaction mixture is 85% or more.

Pure PFP is obtained by filtration of the reaction mixture, acidification to pH 3–7 by aqueous HCl, followed by extraction with one of the following solvents: nBuAc, MIBK, toluene, then fractional distillation.

EXAMPLES 4 AND 5

The preparation of PFP was carried out as described in Example 1, but using CuO as catalyst and under the following conditions and with the results shown in Table II:

aq. (NaOH+Na$_2$CO$_3$)—20%
NaOH/PBFB molar ratio—1.4
Na$_2$CO$_3$/PBFB molar ratio—1.1
PBFB/CuO molar ratio—3.2
Temperature—205±5° C.
Time—4 hours

TABLE II

| Example No. | Composition (GC, area %)* | | | | | F$^-$ in aq. reaction mixture | |
|---|---|---|---|---|---|---|---|
| | FB | PBFB | PFP | DFDPE | FHDPE | ppm | mole % |
| 4 | 1.3 | 0.1 | 93.3 | 3.4 | 1.8 | 880 | 4.8 |
| 5 | 0.8 | 0.3 | 93.8 | 3.5 | 1.4 | 860 | 4.7 |

*PhOH n.d. < 0.1%

EXAMPLES 6 TO 11

The comparative behavior of different catalysts is illustrated by the following hydrolyses shown in Table III:
aq. (NaOH+Na$_2$CO$_3$)—23%
Temperature—205±5° C.
Time—4 hours

TABLE III

| Ex. No. | Molar Ratio NaOH/PBFB | Molar Ratio Na$_2$CO$_3$/PBFB | PBFB/Cat. | Catalyst used | Composition (GC, area %) FB | PBFB | PhOH | PFP | DFDPE | FHDPE |
|---|---|---|---|---|---|---|---|---|---|---|
| 6 | 1.5 | 1.16 | 6.5 | Cu$_2$O | 1.4 | 1.4 | 0.11 | 90.3 | 5.0 | 1.6 |
| 7 | 1.5 | 1.16 | 6.5 |  | 1.1 | 0.6 | 0.12 | 91.7 | 3.2 | 1.4 |
| 8 | 1.5 | 1.16 | 3.6 | CuO | 1.4 | 0.2 | 0.09 | 91.2 | 3.9 | 2.0 |
| 9 | 1.5 | 1.16 | 3.6 |  | 1.7 | 0.3 | 0.09 | 90.8 | 3.9 | 2.0 |
| 10 | 1.6 | 1.20 | 6.0 | CuSO$_4$.5H$_2$O | 1.6 | 0.3 | 0.06 | 89.7 | 4.1 | 3.8 |
| 11 | 1.6 | 1.00 | 6.0 |  | 2.9 | 0.3 | 0.06 | 87.9 | 5.1 | 3.4 |

EXAMPLES 12, 13 AND 14

The following examples, carried out under the following conditions and with the results shown in Table IV, illustrate the effect of temperature variations within the range 205±5° C.
aq. (NaOH+Na$_2$CO$_3$)—20% w/w
NaOH/PBFB molar ratio—1.5
Na$^2$CO$^3$/PBFB molar ratio—1.2
PBFB/CuO molar ratio—13

TABLE IV

| Ex. No. | Temp ° C. | Time hr | Conv. by Br$^-$ % | Composition (GC, area %) FB | PBFB | PhOH | PFP | DFDPE | FHDPE |
|---|---|---|---|---|---|---|---|---|---|
| 12 | 200 | 4.5 | 96.0 | 1.8 | 2.9 | 0.11 | 93.4 | 1.6 | 0.2 |
| 13 | 205 | 4.0 | 97.6 | 1.0 | 0.9 | 0.15 | 95.1 | 2.0 | 0.6 |
| 14 | 210 | 3.0 | 98.5 | — | 0.1 | 0.17 | 97.2 | 1.9 | 0.5 |

The reaction can be carried out at lower and higher temperatures, e.g. from 180 to 220° C. However, as the temperature is lowered, the reaction proceeds more slowly; and as it is increased, more phenol by-product tends to form.

EXAMPLES 15 AND 16

The amounts of bases used can vary within relatively wide limits and still produce satisfactory results, as shown by the following examples in Table V:
aq. (NaOH+Na$_2$CO$_3$)—20% w/w
PBFB/Cu$_2$O molar ratio—13
Temperature—205±5° C.

TABLE V

| Example No. | Molar Ratio NaOH/PBFB | Molar Ratio Na$_2$CO$_3$/PBFB | Conv. by Br$^-$ % | Time hr | Main Impurities PhOH | DFDPE | FHDPE |
|---|---|---|---|---|---|---|---|
| 15 | 1.5 | 1.2 | 96.0 | 4.5 | 0.11 | 1.6 | 0.2 |
| 16 | 0.8 | 1.6 | 98.9 | 3.7 | 0.05 | 3.7 | 4.4 |

The use of $Na_2CO_3$ alone would give small amounts of phenol, but at the expense of large amounts of DFDPE and FHDPE.

EXAMPLES 17 TO 20

The total concentration of the bases in their aqueous solution can also be varied considerably. Non-limitative examples are given in the following shown in Table VI:
NaOH/PBFB molar ratio—1.4
$Na^2CO^3$/PBFB molar ratio—1.1
Temperature—205±5° C.
Time—4 hours

TABLE VI

| | Catalyst | | | Main Impurities | | | |
|---|---|---|---|---|---|---|---|
| Example No. | Type | Molar Ratio PBFB/cat | Conc. of base % | FB | PhOH | DFDPE | FHDPE |
| 17 | $Cu_2O$ | 6.5 | 25 | 2.4 | 0.13 | 6.1 | 3.4 |
| 18 | CuO | 6.5 | 20 | 2.3 | 0.09 | 4.4 | 2.9 |
| 19 | CuO | 3.6 | 25 | 1.5 | 0.11 | 6.2 | 2.5 |
| 20 | CuO | 3.6 | 20 | 1.3 | 0.08 | 3.2 | 1.0 |

The use of a higher concentration of base raises the efficiency of the reactor, but the results show that the higher the base concentration, the lower the selectivity of the hydrolysis for PFP. Higher base concentrations led to the formation of more phenol and heavies (DFDPE and FHDPE).

EXAMPLES 21 TO 23

The ratio of PBFB to catalyst has an influence on the results of the reaction. Examples 21 to 23, shown in Table VII, relate to hydrolyses carried out under the following conditions:

aq. ($NaOH+Na_2CO_3$)—20%
NaOH/PBFB molar ratio—1.5
$Na_2CO_3$/PBFB molar ratio—1.2
Temperature—205±5° C.
Time—4 hours

TABLE VII

| Example No. | PBFB/$Cu_2O$ | Conv. by $Br^-$ % | Composition (GC area %) | | | | | |
|---|---|---|---|---|---|---|---|---|
| | | | FB | PBFB | PhOH | PFP | DFDPE | FHDPE |
| 21 | 20 | 85.3 | 1.5 | 13.9 | 0.18 | 83.0 | 1.0 | 0.1 |
| 22 | 13 | 97.6 | 1.0 | 0.9 | 0.15 | 95.1 | 2.0 | 0.6 |
| 23 | 6 | 99.1 | 0.7 | 0.5 | 0.09 | 95.4 | 2.0 | 1.1 |

A large amount of catalyst produces a faster reaction and less phenol by-product, as shown by the tabulated results.

The following examples illustrate embodiments wherein the invention is carried out in a semi-batch process. By semi-batch process is meant a process in which the NaOH is slowly added to the reaction mass during the course of the reaction.

In the semi-batch process, the water, the $Na_2CO_3$, the PBFB and the catalyst are charged into a reactor, which is sealed and heated to reaction temperature. NaOH solution is then added at a constant flow rate over a few, preferably 3 to 5, hours, whereafter the temperature is maintained for an additional time, e.g. about one hour, to permit the reaction to be completed. When the reaction is carried out in this manner, the preferred catalyst is $Cu_2O$ and the preferred molar ratio of PBFB to $Cu_2O$ is from 4 to 6.3. The reaction temperature is from 200° to 220° C., preferably about 210° C. The preferred molar ratio $Na_2CO_3$/PBFB is 0.25–0.50 and the preferred molar ratio NaOH/PBFB is 1.8–2.2.

EXAMPLE 24

An 8-litre reactor was loaded with 1919 g $H_2O$, 283 g $Na_2CO_3$, 1847 g PBFB and 369 g $Cu_2O$. The mixture was heated to 210° C. 1738 g of 48% NaOH was then slowly added to the reactor by means of a diaphragm pump, the temperature in the reactor being maintained at 210° C. The NaOH was added at a constant flow rate over 5 hours. The temperature was maintained for an additional hour. During this hour, a drop in the pressure of about 1 atm from −20 to 19 atm was observed, which indicated elimination of the vapor pressure of the PBFB and completion of the reaction.

The mixture was then cooled to 70° C. The mixture was filtered to remove the catalyst and the filtration line washed with 1000 g water. The mixture was acidified to pH=6.5 and cooled to ambient temperature. The product was extracted with 1850 g butyl-acetate. A second extraction was then done with 927 g butyl-acetate. The two extracts were mixed together. The total weight of the two extracts was 4017 g.

3941 g of this extract was distilled in two fractions, in a water-heated rotavapor and then in an oil-heated rotavapor. The first distilled fraction weighed 3680 g and had the following composition (GC area %): BuAc: 72.2%, PFP: 27.4%, DFDFE: 0.4%. The PFP assay as detered by acid titration was 26.0%. 85 g of a two-phase mixture of BuAc and water was collected in the trap.

The second distilled fraction weighed 28.6 and had the following concentration: BuAc: 1.3%, PFP: 81.4%, DFDFE: 16%. The PFP assay was of 84.5%.

The recovered PFP in the two distillation fractions gave a yield of 83%, relative to the PBFB feed. The residue of distillation represents 85.3 g. The balance on the distillation was 98%.

EXAMPLES 25–29

The same operations of Example 24 were carried out in the following Examples, but with the amount of reagents and catalyst and the composition of the final product set forth in the following Table VIII.

TABLE VIII

Detailed results of semi-batch reaction in the 8l reactor

| Example No. | PBFB (moles) | Feed Molar ratio | | | $Cu_2O$ (wt %) | Temp. (deg. C) | Composition (GC area %) | | | | | | | |
|---|---|---|---|---|---|---|---|---|---|---|---|---|---|---|
| | | PBFB | NaOH | $Na_2CO_2$ | | | FB | OFP | PBFB | PhOH | PFP | PFPAc | DFDPE | FDHPE |
| 25 | 9.59 | 1 | 2.4 | 0.25 | 20 | 210 | 0.7 | 0.06 | 0.01 | 0.088 | 97.0 | 0.1 | 0.8 | 0.6 |
| 26 | 9.59 | 1 | 2.3 | 0.25 | 20 | 220 | 0.5 | 0.06 | 0.07 | 0.120 | 87.3 | 0.3 | 7.8 | 3.5 |
| 27 | 9.59 | 1 | 2.4 | 0.5 | 20 | 210 | 0.1 | 1.44 | nd | 0.240 | 96.6 | 0.1 | 0.0 | 1.3 |
| 28 | 10.55 | 1 | 2 | 0.25 | 20 | 210 | n.d. | 0.05 | n.d. | 0.082 | 97.9 | 0.2 | 0.5 | 1.0 |
| 29 | 13.4 | 1 | 2.2 | 0.25 | 13 | 210 | 0.2 | 0.08 | n.d. | 0.126 | 97.9 | 0.1 | 0.1 | 1.4 |

The productivity of the process is increased by the semi-batch operation. In Examples 24 to 29 the PBFB loading of the reactor, calculated on the basis of its final content, after NaOH addition, free of catalyst, varied from 16 to 38 wt %.

The process can be carried out, if desired, in a continuous manner.

While embodiments of the invention have been described by way of illustration, it will be apparent that the invention may be carried out by persons skilled in the art with many modifications, variations and adaptations, without departing from its spirit or exceeding the scope of the claims.

We claim:

1. Process for the preparation of p-fluorophenol, which comprises hydrolyzing p-bromofluorobenzene with a mixture of NaOH and $Na_2CO_3$ in the presence of a copper catalyst.

2. Process according to claim 1, wherein the copper catalyst is chosen from among $Cu_2O$, CuO and $CuSO_4 \cdot 5H_2O$.

3. Process according to claim 1, wherein the hydrolysis is carried out at temperatures from 180 to 240° C.

4. Process according to claim 1, wherein the hydrolysis is carried out at temperatures of 200–210° C.

5. Process according to claim 1, wherein the molar ratio of sodium hydroxide to p-bromofluorobenzene is comprised between 0.8 and 2.6.

6. Process according to claim 1, wherein the molar ratio of sodium hydroxide to p-bromofluorobenzene is comprised between 1.4 and 2.4.

7. Process according to claim 1, wherein the molar ratio of sodium carbonate to p-bromofluorobenzene is comprised between 0.25 and 1.6.

8. Process according to claim 1, wherein the molar ratio of sodium carbonate to p-bromofluorobenzene is comprised between 0.25 and 1.2.

9. Process according to claim 1, wherein the sodium hydroxide and the sodium carbonate are used in aqueous solution with a total concentration from 10 to 30%.

10. Process according to claim 9, wherein the sodium hydroxide and the sodium carbonate are used in aqueous solution with a total concentration of 20 to 25% w/w.

11. Process according to claim 2, carried out in batch, wherein the copper catalyst is used in such an amount that the molar ratio of p-bromofluorobenzene to $Cu_2O$ is from 6 to 12 and the molar ratio of p-bromofluorobenzene to CuO is from 3 to 6.

12. Process according to claim 2, carried out in semi-batch, wherein the copper catalyst is $Cu_2O$ and is used in such an amount that the molar ratio of p-bromofluorobenzene to $Cu_2O$ is from 4 to 6.3.

13. Process according to claim 1, carried out in semi-batch, wherein the molar ratio of sodium hydroxide to p-bromofluorobenzene is comprised between 1.8 and 2.2 and the molar ratio of sodium carbonate to p-bromofluorobenzene is comprised between 0.25 and 0.5.

14. Process according to claim 1, carried out in semi-batch, wherein the sodium hydroxide is slowly added to a mixture of p-bromofluorobenzene, sodium carbonate and catalyst, at the reaction temperature and at such a flow rate that the addition lasts from 3 to 5 hours.

15. Process according to claim 14, wherein the reaction mixture is kept at the reaction temperature, after the addition of sodium hydroxide, until the reaction is completed.

16. Process according to claim 1, further comprising subjecting the reaction product to work-up, extraction with a suitable solvent and distillation.

17. Process according to claim 16, wherein the solvent for extraction is chosen from among toluene, n-butyl acetate and methyl isobutyl ketone.

* * * * *

UNITED STATES PATENT AND TRADEMARK OFFICE
CERTIFICATE OF CORRECTION

PATENT NO.   :   6,037,503
DATED        :   March 14, 2000
INVENTOR(S)  :   Oren et al.

It is certified that error appears in the above-identified patent and that said Letters Patent is hereby corrected as shown below:

Col. 7, line 11, "Na$^2$CO$^3$" should read -- Na$_2$CO$_3$--.

Col. 7, in Table VI, line 23, "CuO" should read --Cu$_2$O--.

Col. 9, line 15, "detered" should read --determined--.

Col. 9, line 20, after "28.6" insert --g--.

Cols. 9 and 10, in Table VIII, under Example No. 27, "nd" should read --n.d.--

Signed and Sealed this

Twenty-seventh Day of February, 2001

Attest:

NICHOLAS P. GODICI

Attesting Officer

Acting Director of the United States Patent and Trademark Office